(12) United States Patent
Obara et al.

(10) Patent No.: US 7,989,042 B2
(45) Date of Patent: Aug. 2, 2011

(54) MEDICAL DEVICES WITH HIGHLY FLEXIBLE COATED HYPOTUBE

(75) Inventors: Robert Z. Obara, Fremont, CA (US); Gregory E. Mirigian, Dublin, CA (US); Huey Quoc Chan, San Jose, CA (US); John E. Ortiz, East Palo Alto, CA (US); Stephen Griffin, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 500 days.

(21) Appl. No.: 10/996,976

(22) Filed: Nov. 24, 2004

(65) Prior Publication Data

US 2006/0121218 A1    Jun. 8, 2006

(51) Int. Cl.
*A61B 5/00* (2006.01)
*A61M 25/00* (2006.01)

(52) U.S. Cl. ....... 428/36.9; 427/2.1; 428/35.7; 428/364; 528/26; 600/300; 600/585; 623/1.15

(58) Field of Classification Search ................. 428/36.9, 428/35.7, 364; 623/1.15; 600/585, 300; 528/26; 427/2.1
See application file for complete search history.

(56) References Cited

U.S. PATENT DOCUMENTS

| | | | |
|---|---|---|---|
| 3,174,851 A | 3/1965 | Bushler et al. | |
| 3,351,463 A | 11/1967 | Rozner et al. | |
| 3,753,700 A | 8/1973 | Harrison et al. | |
| 4,261,286 A | 4/1981 | Kupfer | |
| 4,503,801 A | 3/1985 | Collishaw et al. | |
| 4,547,193 A | 10/1985 | Rydell | |
| 4,949,667 A | 8/1990 | Yoshida et al. | |
| 4,960,410 A | 10/1990 | Pinchuk | |
| 4,998,923 A | 3/1991 | Samson et al. | |
| 5,238,004 A | 8/1993 | Sahatjian et al. | |
| 5,397,306 A | 3/1995 | Nobuyoshi et al. | |
| 5,437,288 A | 8/1995 | Schwartz et al. | |
| 5,507,766 A | 4/1996 | Kugo et al. | |
| 5,531,719 A | 7/1996 | Takahashi | |
| 5,569,200 A | 10/1996 | Umeno et al. | |
| 5,573,520 A | 11/1996 | Schwartz et al. | |
| 5,690,120 A | 11/1997 | Jacobsen et al. | |
| 5,741,429 A * | 4/1998 | Donadio et al. | 216/8 |
| 5,772,609 A | 6/1998 | Nguyen et al. | |
| 5,827,201 A * | 10/1998 | Samson et al. | 600/585 |

(Continued)

FOREIGN PATENT DOCUMENTS

JP          60012069          1/1985

(Continued)

OTHER PUBLICATIONS

"What is Paralene?", Paralene.com, Oct. 19, 2004, 4 pgs., http://www.paralene.com/paralene_coating.htm.

(Continued)

*Primary Examiner* — Brent T O'Hern
(74) *Attorney, Agent, or Firm* — Seager, Tufte & Wickhem LLC

(57) ABSTRACT

Hypotubes such as micromachined hypotubes can include one or more tie layers appropriate for subsequent application of a hydrophilic coating. In particular, a medical device may include a micromachined hypotube having a level of flexibility and a tie layer disposed over the hypotube such that the medical device has a level of flexibility at least substantially equivalent to the level of flexibility of the hypotube.

11 Claims, 7 Drawing Sheets

U.S. PATENT DOCUMENTS

| | | | |
|---|---|---|---|
| 5,938,623 | A | 8/1999 | Quiachon et al. |
| 6,014,919 | A | 1/2000 | Jacobsen et al. |
| 6,017,319 | A | 1/2000 | Jacobsen et al. |
| 6,102,890 | A | 8/2000 | Stivland et al. |
| 6,238,376 | B1 | 5/2001 | Peterson |
| 6,306,124 | B1 | 10/2001 | Jones et al. |
| 6,313,254 | B1 * | 11/2001 | Meijs et al. ............... 528/26 |
| 6,329,488 | B1 | 12/2001 | Terry et al. |
| 6,420,452 | B1 | 7/2002 | Gunatillake et al. |
| 6,428,489 | B1 | 8/2002 | Jacobsen et al. |
| 6,437,073 | B1 | 8/2002 | Gunatillake et al. |
| 6,440,088 | B1 | 8/2002 | Jacobsen et al. |
| 6,508,803 | B1 | 1/2003 | Horikawa et al. |
| 6,627,724 | B2 | 9/2003 | Meijs et al. |
| 6,638,267 | B1 | 10/2003 | Esselstein et al. |
| 6,652,508 | B2 * | 11/2003 | Griffin et al. ............ 604/526 |
| 2003/0009208 | A1 | 1/2003 | Snyder et al. |
| 2003/0018156 | A1 | 1/2003 | Maijs et al. |
| 2003/0060732 | A1 | 3/2003 | Jacobsen et al. |
| 2003/0069522 | A1 | 4/2003 | Jacobsen et al. |
| 2003/0093059 | A1 | 5/2003 | Griffin et al. |
| 2003/0114776 | A1 | 6/2003 | Griffin et al. |
| 2003/0125709 | A1 | 7/2003 | Eidenschink |
| 2003/0181827 | A1 * | 9/2003 | Hojeibane et al. ........... 600/585 |
| 2004/0054322 | A1 | 3/2004 | Vargas |
| 2004/0059409 | A1 * | 3/2004 | Stenzel ................ 623/1.15 |
| 2004/0111044 | A1 | 6/2004 | Davis et al. |
| 2004/0181174 | A2 | 9/2004 | Davis et al. |
| 2005/0102017 | A1 | 5/2005 | Mattison |
| 2005/0165439 | A1 | 7/2005 | Weber et al. |

FOREIGN PATENT DOCUMENTS

| | | |
|---|---|---|
| WO | 95/24236 A1 | 9/1995 |
| WO | 0216974 A2 | 2/2002 |
| WO | 2006009985 A1 | 1/2006 |

OTHER PUBLICATIONS

"Synchro® Microfabricated Nitinol Guidewires" Fact Sheet, 3 pgs.. Boston Scientific Corporation.

Synchro® Microfabricated Nitinol Guidewires, Neuro/Peripheral Interventions, Oct. 19, 2004, 2 pgs., Boston Scientific Corporation, http://www.bostonscientific.com/med_specialty/deviceDetail.jhtmal?task=tskBasicDevice.

"Torque Transmission", Oct. 19, 2004, 1 pg., Boston Scientific Corporation, http://www.bostonscientific.com/templatedata/imports/multimedica/Neuro/dph_synchro_4.

Skalsky, "High Siloxane Content Polyurethanes for Implantable Devices", MP 2001 Speakers, 2 pgs., Sep. 28, 2004, http://www.hexagon.dk/pages/Proceedings/MP2001%20Speakers/M_Skalsky.htm.

"Elast-Eon™ Technology", 2 pgs., Sep. 28, 2004, http://www.aortech.com/technology.asp.

* cited by examiner

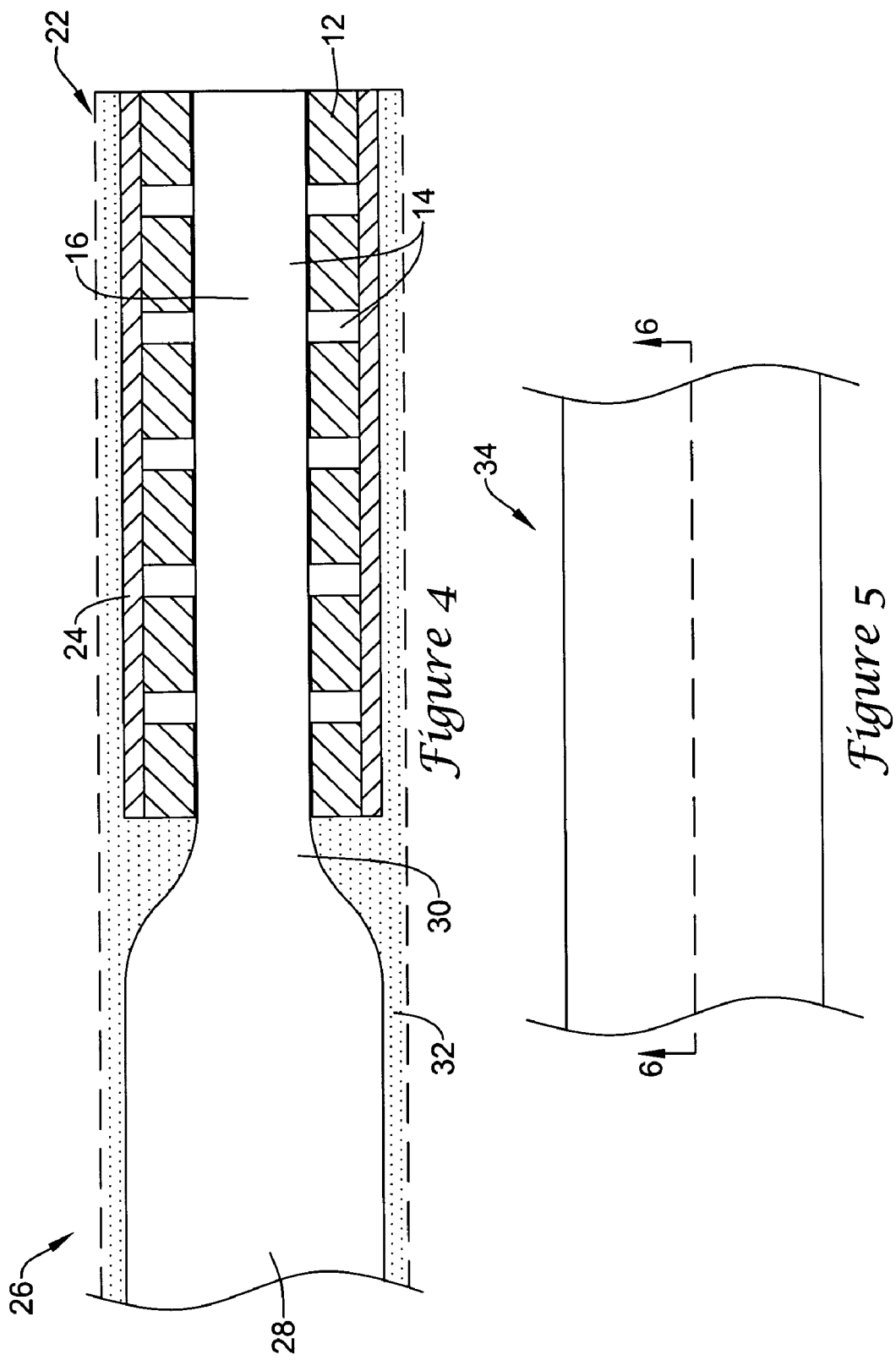

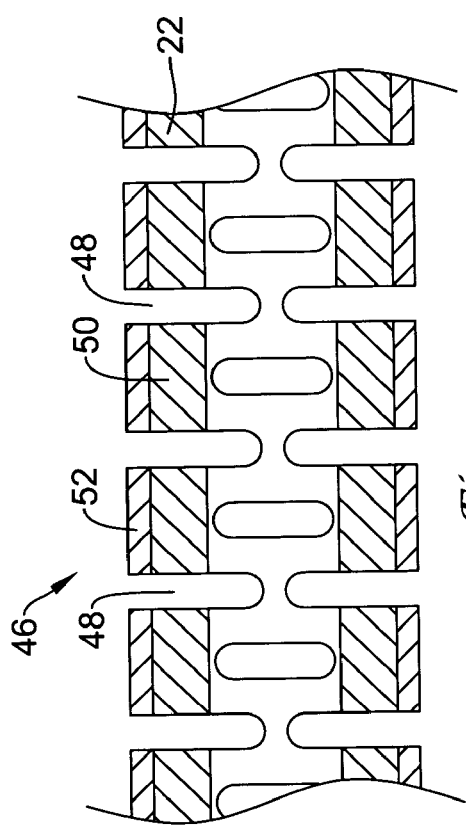
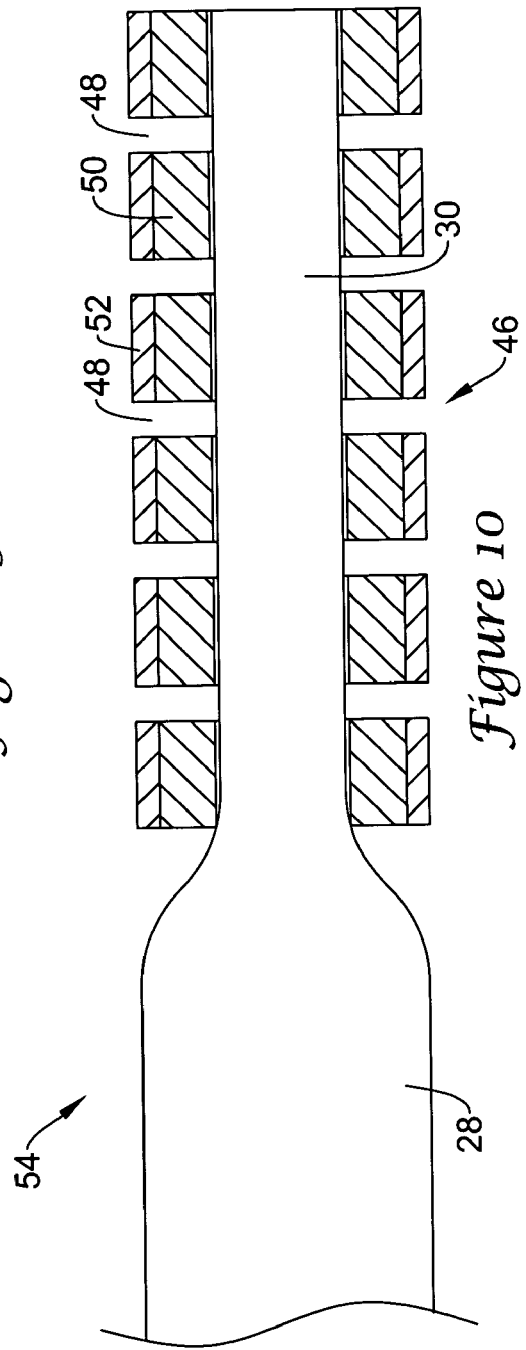
Figure 9
Figure 10

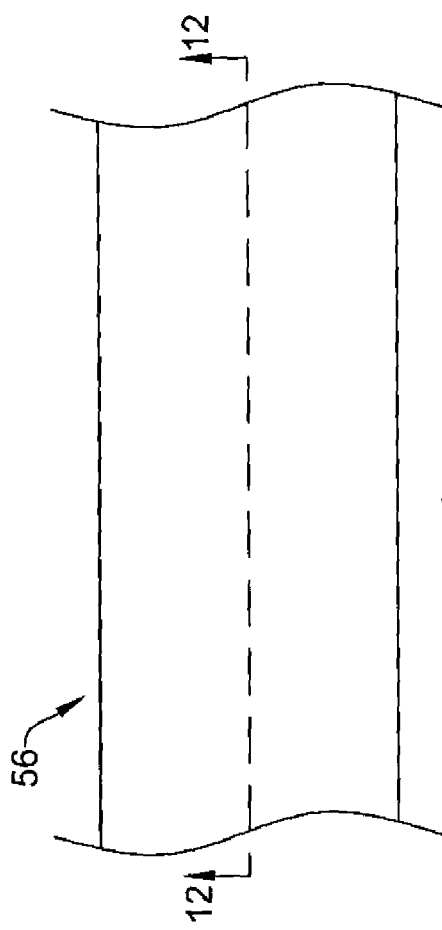
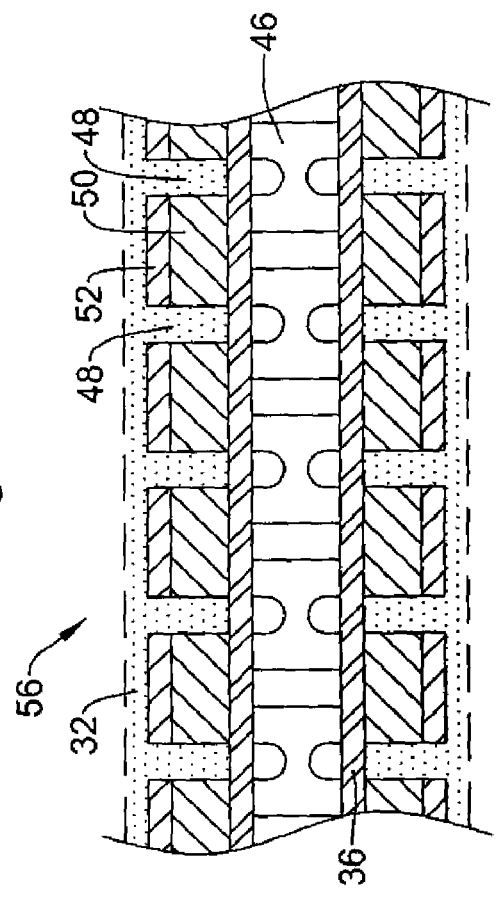

MEDICAL DEVICES WITH HIGHLY FLEXIBLE COATED HYPOTUBE

TECHNICAL FIELD

The invention pertains generally to medical devices and more specifically to medical devices that include or are formed from a hypotube. In particular, the invention pertains to medical devices that include a highly flexible coated hypotube.

BACKGROUND

A number of medical devices, including elongated medical devices such as catheters and guidewires, are known. Such devices can include or be formed from a hypotube. In some cases, a number of slots can be formed in the hypotube to improve the flexibility of the hypotube. The resulting product is sometimes referred to as a micromachined hypotube.

A hypotube such as a micromachined hypotube may be subjected to one or more coating processes to provide the micromachined hypotube with a hydrophilic coating that lends biocompatibility and lubricity to the hypotube. As many hydrophilic coatings do not adequately adhere to many metals, a tie layer is oftentimes provided prior to forming the hydrophilic coating.

Unfortunately, a tie layer may negatively impact the flexibility of a micromachined hypotube by, for example, limiting relative movement between adjacent turnings or portions of the hypotube. Therefore, a need remains for improved tie layers that provide sufficient support for an overlaying hydrophilic coating. A need also remains for improved tie layers that do not negatively impact the flexibility of the micromachined hypotube.

SUMMARY

The present invention pertains to micromachined hypotubes that include one or more tie layers appropriate for subsequent application of a hydrophilic coating while retaining the flexibility of the micromachined hypotube.

Accordingly, an illustrative embodiment of the invention may be found in a medical device that includes a micromachined hypotube having a level of flexibility and a tie layer disposed over the hypotube such that the medical device has a level of flexibility at least substantially equivalent to the level of flexibility of the hypotube.

Another illustrative embodiment of the invention may be found in a medical device that includes a metallic substrate, an elastomeric tie layer that includes a polysiloxane-containing polyurethane, and a hydrophilic coating disposed on the tie layer.

Another illustrative embodiment of the invention may be found in a medical device that includes a micromachined hypotube that has an outer surface. The outer surface of the hypotube includes a plurality of radially aligned voids and a plurality of surface elements disposed between adjacent voids. The medical device also includes a tie layer that is disposed over the micromachined hypotube such that the tie layer contacts at least most of the plurality of surface elements but does not cover at least some of the voids.

Another illustrative embodiment of the invention may be found in a method of forming a tie layer on a micromachined hypotube that includes a plurality of radially aligned voids and a plurality of surface elements that are disposed between adjacent voids. A source of liquid polymer is provided, and a roller is contacted with the liquid polymer. The micromachined hypotube is then contacted with the roller bearing the liquid polymer to form the tie layer. The resulting tie layer is in contact with at least some of the plurality of surface elements but does not cover at least some of the plurality of voids.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which:

FIG. 4 is a view of a portion of a guidewire bearing the micromachined hypotube of FIG. 2;

FIG. 5 is a view of a portion of a catheter including the micromachined hypotube of FIG. 2, seen with an optional inner liner;

FIG. 9 is an axial cross-section taken along line 9-9 of FIG. 8;

FIG. 10 is a view of a portion of a guidewire bearing the coated micromachined hypotube of FIG. 8;

FIG. 11 is a view of a portion of a catheter including the coated micromachined hypotube of FIG. 8, seen with an optional inner liner; and FIG. 12 is an axial cross-section taken along line 12-12 of FIG. 11.

Figure 1:
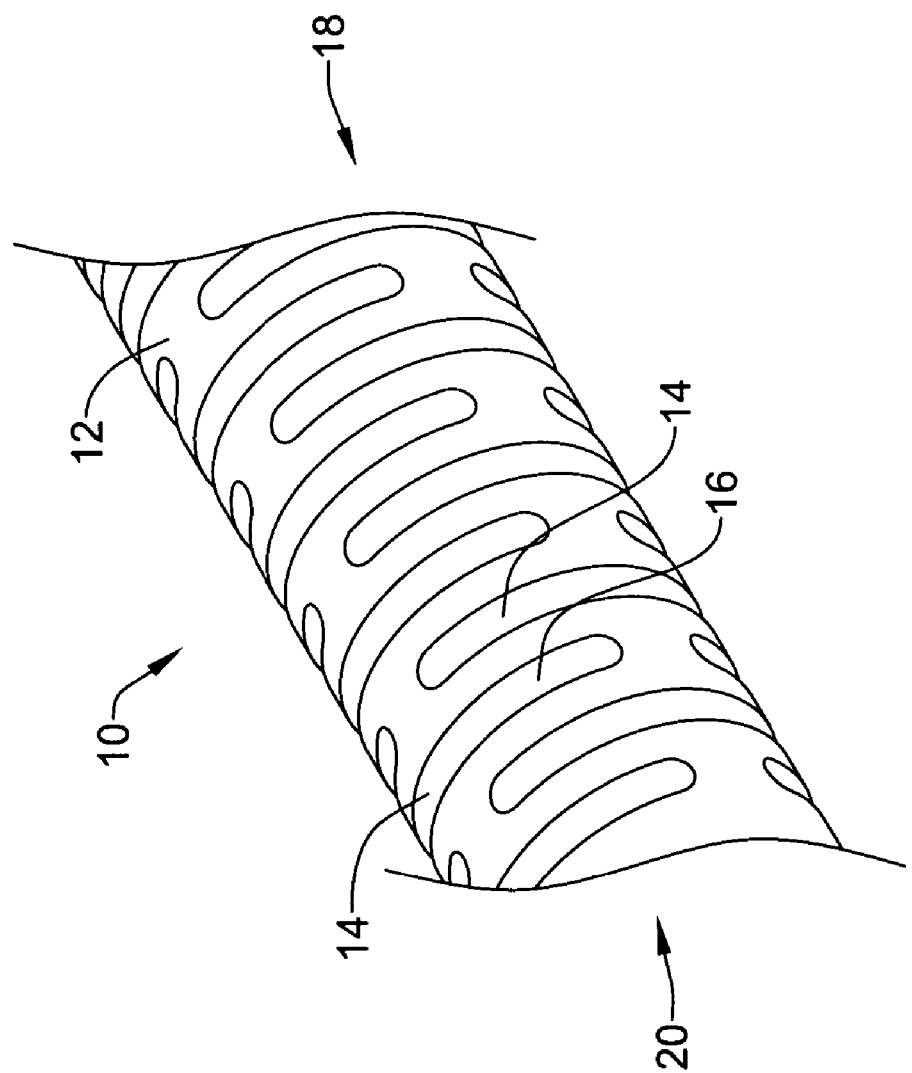
FIG. 1 is a perspective view of a micromachined hypotube in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value, i.e., having the same function or result. In many instances, the term "about" may include numbers that are rounded to the nearest significant figure.

As used in this specification and in the appended claims, the singular forms "a", "an", and "the" include plural referents unless the content clearly dictates otherwise. As used in this specification and in the appended claims, the term "or" is generally employed in its sense including "and/or" unless the content clearly dictates otherwise.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

The invention pertains generally to medical devices that include a hypotube such as a micromachined hypotube. Such medical devices may include guidewires and microcatheters.

Turning now to FIG. 1, a perspective view of an illustrative micromachined hypotube 10 is seen. The hypotube 10 includes an elongate body 12 having a plurality of slots 14 cut into the elongate body 12. In some embodiments, as illustrated, the slots 14 may be radially oriented. Although the slots 14 do not extend all the way around a circumference of the elongate body 12, it can be seen that adjacent slots 14 define voids on either side of a surface element 16. As illustrated in FIG. 1, the slots 14 are substantially perpendicular to the axial direction of the hypotube 10 with adjacent slots 14 having distal ends that are substantially semicircular in shape and project in opposite directions along a circumference of the hypotube 10.

The slots 14 may be formed in any suitable manner. For example, in some embodiments, the slots 14 are formed via laser cutting. In other instances, the slots 14 may be formed by saw cutting, abrasion, or any other known cutting or grinding mechanism. The slots 14 can be dimensioned and located to provide a desired level of flexibility. In some instances, the slots 14 may be equally spaced from a distal portion 18 to a proximal portion 20. In other cases, the slots 14 may be, for example, more closely spaced together near the distal portion 18 for additional flexibility and more spaced apart near the proximal portion 20 for additional strength. In an illustrative but non-limiting embodiment, the slots 14 may have a width that is in the range of about 0.0005 inches to about 0.020 inches. Each slot 14 may extend about ten percent, about twenty percent, about thirty percent, about forty percent, about fifty percent, about sixty percent, about seventy percent, about eighty percent, about ninety percent or more about the circumference of the elongate body 12.

The hypotube 10 may have any suitable dimensions, depending on an ultimate use thereof. In some cases, the hypotube 10 can have an overall length that is in the range of about 30 centimeters to about 300 centimeters. The hypotube 10 may have an outer diameter that is in the range of about 0.008 inches to about 0.156 inches, a wall thickness that is in the range of about 0.001 inches to about 0.02 inches, and a resulting inner diameter that is in the range of about 0.006 inches to about 0.0116 inches.

The elongate body 12 may be formed of any suitable metallic, polymeric or composite material. In some embodiments, part or all of the elongate body 12 can be formed of a metal or a metal alloy. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 825; or the like; or other suitable material. The particular material used can be chosen in part based on the desired characteristics of the elongate body 12, for example flexability, pushability, torqueability, and the like.

As indicated above, in some particular embodiments, the elongate body 12 can be formed from a superelastic or linear elastic nickel-titanium alloy, for example, linear elastic or superelastic (i.e. pseudoelastic) nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys, is a category designated "linear elastic" which, although is similar in chemistry to conventional shape memory and superelastic varieties, exhibits distinct and useful mechanical properties. By skilled applications of cold work, directional stress, and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there is no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel-titanium alloys include those disclosed in U.S. Pat. Nos. 5,238,004 and 6,508,803, which are incorporated herein by reference.

Figure 2:
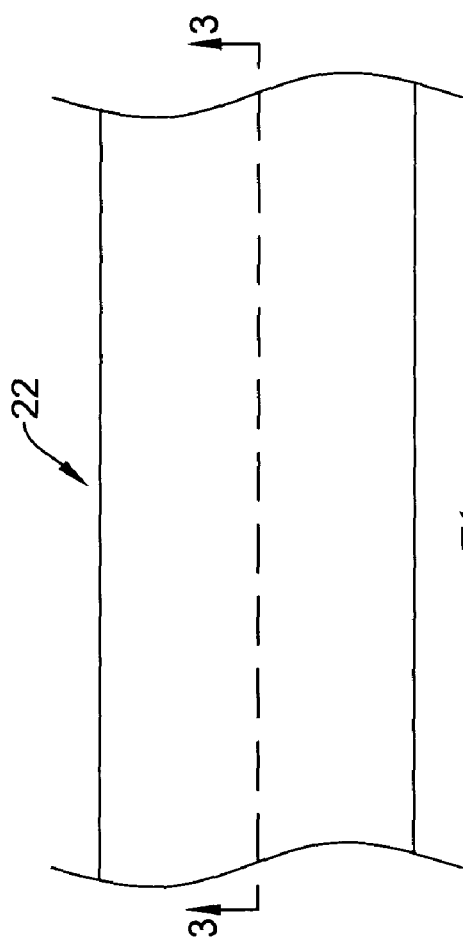
FIG. 2 is a view of the micromachined hypotube of FIG. 1, including a continuous tie layer applied to an exterior surface of the hypotube in accordance with an embodiment of the invention.
Figure 3:
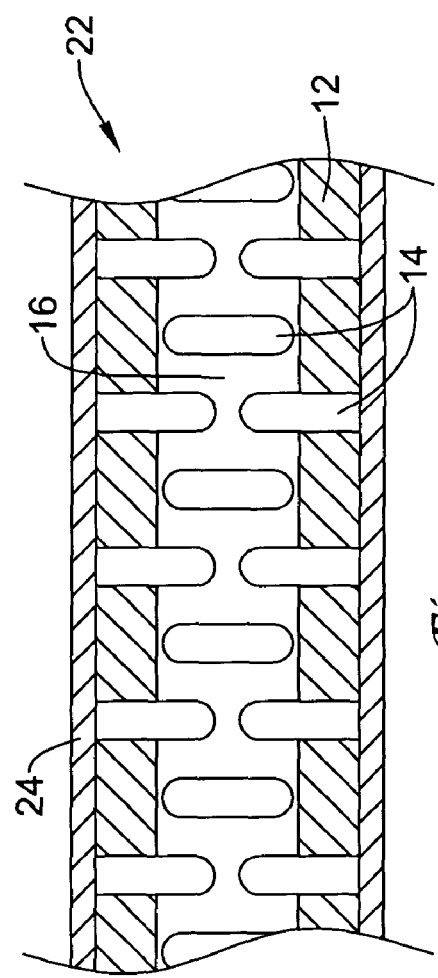
FIG. 3 is an axial cross-section taken along line 3-3 of FIG. 2.

FIG. 2 is a schematic illustration of a coated hypotube 22. In some cases, coated hypotube 22 may represent the hypotube 10 (FIG. 1) with a polymer layer disposed over an outer surface of the hypotube 10. The polymer layer 24 is best seen in FIG. 3, which is an axial cross-section taken along line 3-3 of FIG. 2. In some embodiments, the polymer layer 24 can represent a tie layer that is capable of bonding to the material used to form the hypotube 10. In particular embodiments, the tie layer can be formed from a material that is capable of bonding to nickel/titanium alloys such as the nitinol alloys discussed above.

The polymer layer 24 may be applied to the hypotube 10 in any suitable manner. In some instances, the polymer layer 24 may be spray coated or dip coated onto the hypotube 10. In some embodiments, the polymer layer 24 may be at least substantially continuous, i.e. the polymer layer 24 covers at least substantially all of the surface elements 16 (FIG. 1) as well as at least substantially all of the slots 14 (FIG. 1). It is contemplated, however, that the polymer layer 24 may also be at least partially discontinuous, i.e. perhaps at least some of the slots 14 remain uncovered.

The polymer layer 24 may be formed of any suitable polymeric material. In particular embodiments, the polymer layer 24 is formed of a material such as the ELAST-EON™ materials commercially available from AORTECH BIOMATERIALS, of Australia. The ELAST-EON™ materials generally are polyurethanes that include a polysiloxane component. While these materials encompass both elastomeric and non-elastomeric polymers, elastomeric polymers are useful in particular embodiments of the present invention. In some instances, useful elastomeric polymers may exhibit an elongation of at least about 500 percent.

In some instances, the ELAST-EON™ materials may encompass elastomeric polyurethanes that include significant amounts of a polysiloxane and either a polyether, a polycarbonate, or both a polyether and a polycarbonate. Exemplary materials are described for example in U.S. Pat. No. 6,627, 724, the contents of which are expressly incorporated by reference herein. These materials may be heat-cured to form the polymer layer 24. In some instances, the polymer layer 24 may have a thickness that is about 4 microns or less.

Suitable polysiloxanes include those of the formula:

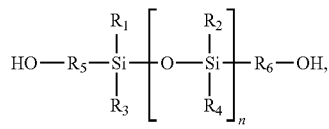

where $R_1$, $R_2$, $R_3$, $R_4$, $R_5$ and $R_6$ can each independently be hydrocarbon radicals and n is an integer that can range from 1 to 100. An exemplary polysiloxane is a compound of the above formula in which $R_1$, $R_2$, $R_3$ and $R_4$ are each methyl. $R_5$ and $R_6$ can each independently be selected from propylene, butylene, pentylene, hexylene, ethoxypropyl, propoxypropyl and butoxypropyl. Polysiloxane may be obtained commercially from Shin Etsu or prepared according to known methods.

Suitable polyethers include those represented by the formula:

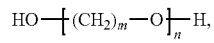

where m can be an integer of at least 4 and in particular may be 5 to 18, and n can be an integer in the range of 2 to 50. Examples of suitable polyethers include polyhexamethylene oxide, polyheptamethylene diol, polyoctamethylene oxide and polydecamethylene oxide.

Suitable polycarbonate macrodiols include poly(alkylene carbonates) such as poly(hexamethylene carbonate) and poly (decamethylene carbonate); polycarbonates prepared by reacting alkylene carbonate with alkanediols for example 1,4-butanediol, 1,10-decandiol, 1,6-hexanediol and/or 2,2-diethyl 1,3-propanediol; and silicon based polycarbonates prepared by reacting alkylene carbonate with 1,3-bis (4-hydroxybutyl)-1,1,3,3-tetramethyldisiloxane and/or alkanediols.

It should be noted that in some cases, the polyether and polycarbonate may be present as a mixture or a copolymer. For example, a suitable copolymer is a copoly(ether carbonate) of the formula:

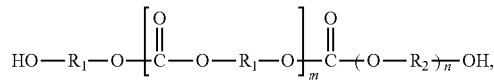

where $R_1$ and $R_2$ are each independently be hydrocarbon radicals, and m and n are each integers ranging from 1 to 20.

These materials may be formed using any suitable technique. In one method, the polysiloxane, polyether and/or polycarbonate and chain extender are mixed together and then the mixture is reacted with a diisocyanate. In another method, a diisocyanate may be reached with the polysiloxane and polyether and/or polycarbonate to form a prepolymer that is subsequently reacted with a chain extender.

Examples of suitable diisocyanates include 4,4'-methylenediphenyl diisocyanate, methylene bis (cyclohexyl) diisocyanate, p-phenylene diisocyanate, trans-cyclohexane-1,4-diisocyanate or a mixture of the cis and trans isomers, 1,6-hexamethylene diisocyanate, 2,4-toluene diisocyanate or its isomers or mixtures thereof, p-tetramethylxylene diisocyanate and m-tetramethylxylene diisocyanate.

Examples of suitable chain extenders include 1,4-butanediol, 1,6-hexanediol, 1,8-octanediol, 1,9-nonadiol, 1,10-decanediol 1,4-cyclohexane dimethanol, p-xyleneglycol, 1,4-bis (2-hydroxyethoxy) benzene and 1,12-dodecanediol.

Figure 6:
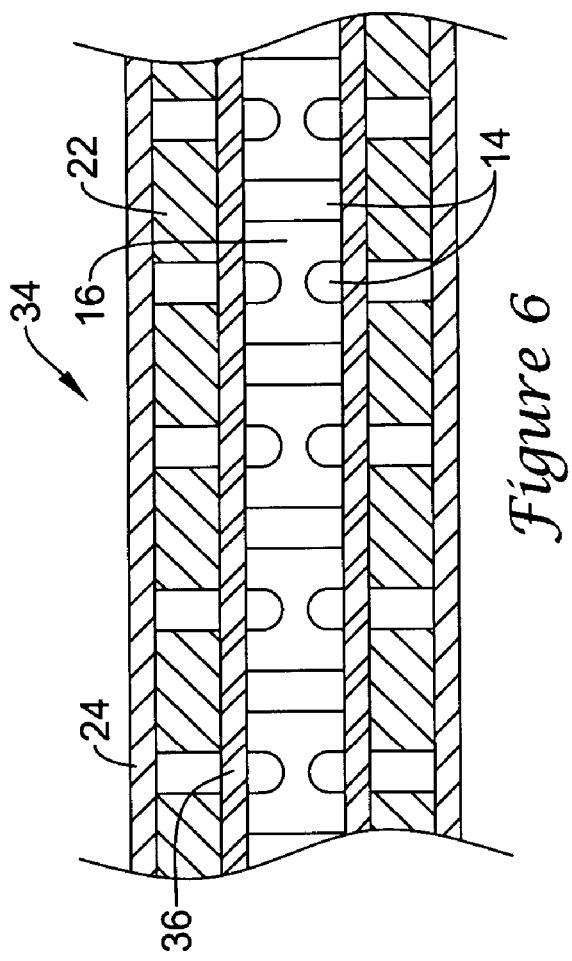
FIG. 6 is an axial cross-section taken along line 6-6 of FIG. 5.

A coated hypotube 22 (FIG. 3) may be employed in a variety of medical devices. Exemplary uses of a coated hypotube 22 includes guidewires and catheters such as microcatheters. FIG. 4 illustrates an exemplary guidewire while FIGS. 5 and 6 illustrate an exemplary catheter.

Turning now to FIG. 4, a distal portion of a guidewire 26 is shown. The guidewire 26 includes a core 28 that narrows down to a tapered portion 30. The coated hypotube 22 may be disposed over the tapered portion 30. The core 28 may be formed of any suitable material and may be constructed using any known techniques for forming guidewire cores. In some instances, the core 28 can be formed from stainless steel or perhaps a nickel/titanium alloy such as Nitinol (previously discussed). The coated hypotube 22 can be secured to the core 28 using any known attachment technique, such as welding.

It is to be appreciated that various welding processes can be utilized. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, microplasma welding, electron beam, and friction or inertia welding.

LASER welding equipment that may be suitable in some embodiments is commercially available from Unitek Miyachi of Monrovia, Calif. and Rofin-Sinar Incorporated of Plymouth, Mich. Resistance welding equipment that may be useful in some embodiments is commercially available from Palomar Products Incorporated of Carlsbad, Calif. and Polaris Electronics of Olathe, Kans. TIG welding equipment that may be useful in some embodiments is commercially available from Weldlogic Incorporated of Newbury Park, Calif. Microplasma welding equipment that may be useful in some embodiments is commercially available from Process Welding Systems Incorporated of Smyrna, Tenn.

Once the guidewire 26 has been formed by securing the coated hypotube 22 to the core 28, the guidewire 26 may receive an optional hydrophilic coating 32. The hydrophilic coating 32 may include or be formed from a polymer that attracts or binds water molecules when the polymer is placed in contact with an aqueous system. Examples of aqueous systems that can provide water molecules that can bind to a hydrophilic polymer include blood and other bodily fluids. When a hydrophilic polymer comes into contact with such a system, water molecules can bind to the polymer via mechanisms such as hydrogen bonding between the water molecules and substituents or functional groups present within or on the polymer. In some instances, a hydrophilic polymer can bind at least 2 times its own weight in water and in particular instances some hydrophilic polymers can bind up to about 20 times their own weight in water.

In some embodiments, hydrophilic polymers such as polyarylene oxides, polyvinylpyrolidones, polyvinylalcohols, hydroxy alkyl cellulosics, algins, saccharides, caprolactones, and the like, and mixtures and combinations thereof, may be used. In some embodiments, the more distal portion of the guidewire is coated with a hydrophilic polymer as discussed above, and the more proximal portions is coated with a fluoropolymer, such as polytetrafluroethylene (PTFE).

In particular instances, the hydrophilic coating 32, if present, can be formed from a hydrophilic material such as HYDROPASS™ or HYDROLENE™. These materials are commercially available from Boston Scientific Corporation and Surmodics. In some cases, the hydrophilic coating 32 may only cover the coated hypotube 22, as the tie layer 24 may in some instances provide a superior base for the hydrophilic coating 32. In other cases, the hydrophilic coating 32 may extend proximally onto at least a portion of the core 28.

While not expressly illustrated, the guidewire 26 may include additional structure and elements commonly incorporated into guidewires. Examples of such elements include one or more polymeric layers, one or more coils or springs, an atraumatic tip, and the like.

The coated hypotube 22 (FIG. 3) may also be used in medical devices such as catheters. Turning now to FIG. 5, a portion of a catheter 34 is illustrated. FIG. 6 is an axial cross-section taken along line 6-6 of FIG. 5. In FIG. 6, the catheter 34 can be seen to include the coated hypotube 22 bearing the tie layer 24, as previously discussed. In some embodiments, as illustrated, the catheter 34 may optionally include an inner polymeric layer 36. The inner polymeric layer 36 may be included to provide a smooth, low-resistance lumen suitable for passing a guidewire or other medical device.

The inner polymeric layer 36 may, if present, be formed of any suitable polymeric material. Examples of suitable materials include polyether block amide, polybutylene terephthalate/polybutylene oxide copolymers sold under the Hytrel® and Arnitel® trademarks, Nylon 11, Nylon 12, polyurethane, polyethylene terephthalate, polyvinyl chloride, polyethylene naphthalene dicarboxylate, olefin/ionomer copolymers, polybutylene terephthalate, polyethylene naphthalate, ethylene terephthalate, butylene terephthalate, ethylene naphthalate copolymers, polyamide/polyether/polyester, polyamides, aromatic polyamides, polyurethanes, aromatic polyisocyanates, polyamide/polyether, and polyester/polyether block copolymers, among others.

In particular embodiments, it may be desirable for inner polymeric layer 36, if present, to be formed of a material having a low coefficient of friction. Suitable materials include fluoropolymers such as polytetrafluoroethylene (PTFE), better known by its tradename of TEFLON®.

Figure 7:
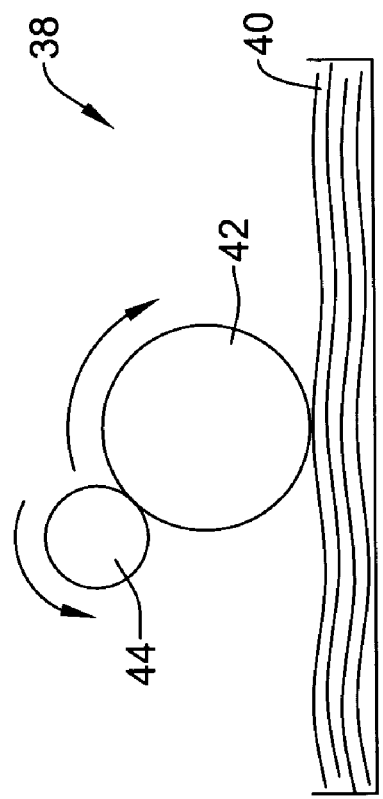
FIG. 7 is a diagrammatic view of a coating apparatus in accordance with an embodiment of the invention.

FIG. 7 diagrammatically illustrates a method of coating a medical device. In FIG. 7, there is provided a coating apparatus 38 that includes a bath 40 containing a liquid polymer material. A transfer roller 42 is in at least partial contact with the polymer within the bath 40, and thereby bears at least some polymer on an outer surface of the transfer roller 42. The transfer roller 42 is also in contact with a medical device 44. In some embodiments, the transfer roller 42 is rotated in a first direction while the medical device 44 is rotated in a second, opposite, direction.

As illustrated, the transfer roller 42 rotates in a clock-wise direction while the medical device 44 rotates in a counter-clockwise-direction, although these directions may of course be reversed. In some embodiments, if a thicker polymer layer is desired on the medical device 44, the transfer roller 42 and the medical device 44 may both rotate in the same direction, or perhaps the transfer roller 42 can rotate while the medical device 44 is held stationary.

Any suitable polymer may be applied using the coating apparatus 38. In some embodiments, the coating apparatus 38 may be used to apply a tie layer made from silane ($SiH_4$), polyacrylic acid (PAA), or paralene. Paralene is available in several different monomers, each of which are shown below:

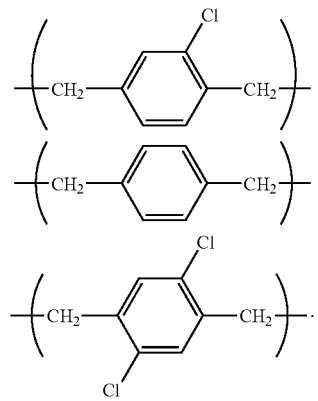

In some instances, a suitable material for forming the tie layer is poly(styrene-b-isobutylene-b-styrene), or SIBS. This material is commercially available from Boston Scientific Corporation under the tradename TRANSLUTE™. This is a hydrophobic elastomeric tri-block copolymer that is based upon 1,3-di(2-methoxy-2-propyl)-5-tert-butylbenzene). SIBS has a number-average molecular weight of about 80,000 to 130,000 grams per mole. Once the medical device 44 has been coated, any suitable or necessary processing steps such as curing steps may be carried out as conventionally known.

An advantage of using the coating apparatus 38 is that in some cases, a medical device such as a micromachined hypotube 10 (FIG. 1) or a medical device including a micromachined hypotube 10 may be coated in such a way as to not cover or plug the radially aligned voids 14 (FIG. 1) present within the micromachined hypotube 10. In some embodiments, the coating apparatus 38 may provide a discontinuous polymeric layer that covers at least some of the surface elements 16 (FIG. 1) but leaves at least some of the radially aligned voids 14 devoid of covering.

Figure 8:
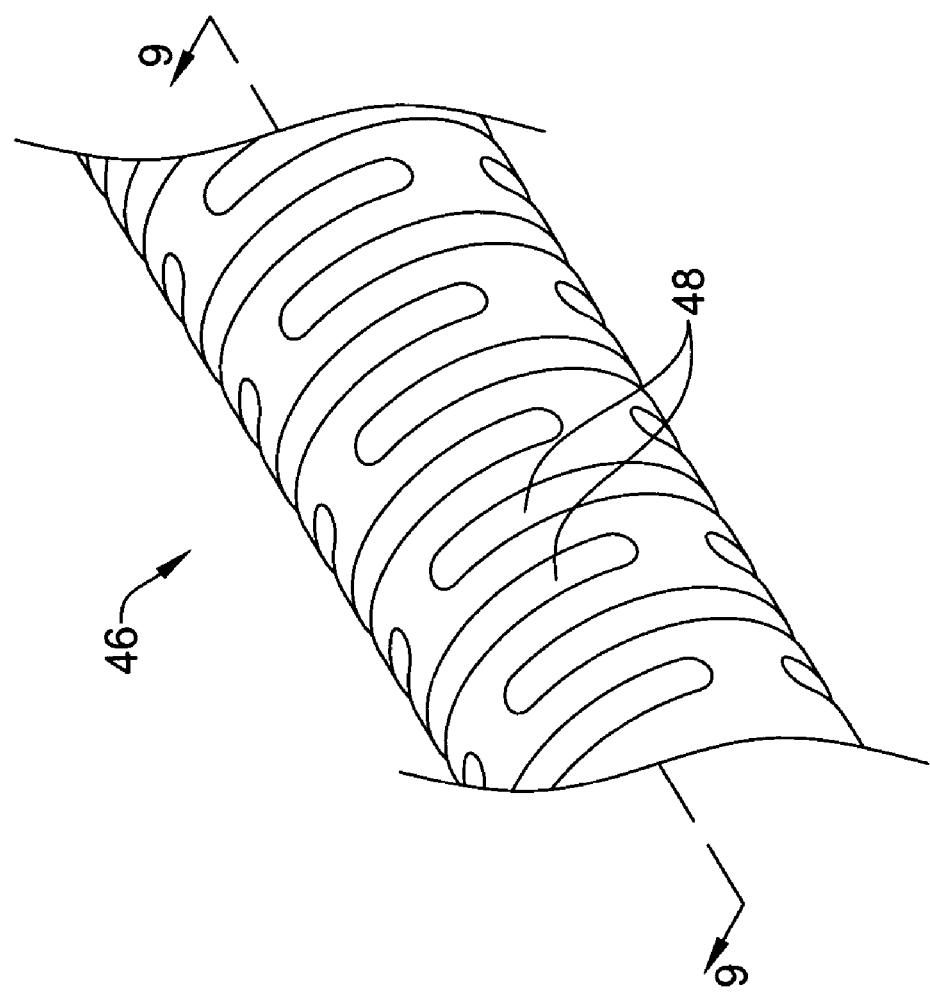
FIG. 8 is a perspective view of a micromachined hypotube coated using the coating apparatus of FIG. 7.

FIG. 8 is a perspective view of a portion of a coated hypotube 46. It can be seen that although the hypotube 46 has been coated, it retains at least some of the radially aligned voids 48 separated by surface elements 50 that have been coated. In some cases, virtually all of the radially aligned voids 48 remain devoid of coating while in other embodiments, a certain percentage of the radially aligned voids 48 may be allowed to be at least partially covered.

The structure of the coated hypotube 46 is better seen in FIG. 9, which is an axial cross-section taken along the 9-9 line of FIG. 8. FIG. 9 clearly illustrates how a coating 52 covers at least some of the surface elements 50 while leaving at least some of the radially aligned voids 48 devoid of covering. In the illustrated embodiment, the coating 52 covers all or virtually all of the surface elements 50 while leaving all or virtually all of the radially aligned voids 48 free of covering.

A coating hypotube 46 (FIG. 8) may be employed in a variety of medical devices. Exemplary uses of a coated hypotube 46 includes guidewires and catheters such as microcatheters. FIG. 10 illustrates an exemplary guidewire while FIGS. 11 and 12 illustrate an exemplary catheter.

Turning now to FIG. 10, a distal portion of a guidewire 54 is shown. The guidewire 54 includes a core 28 that narrows down to a tapered portion 30. The coated hypotube 46 may be disposed over the tapered portion 30. The core 28 may be formed of any suitable material and may be constructed using any known techniques for forming guidewire cores. In some instances, the core 28 can be formed from stainless steel or perhaps a nickel/titanium alloy such as Nitinol (previously discussed). The coated hypotube 46 can be secured to the core 28 using any known attachment technique, such as those discussed with respect to FIG. 4.

While not expressly illustrated, the guidewire 54 may include additional structure and elements commonly incorporated into guidewires. Examples of such elements include one or more polymeric layers, one or more coils or springs, an atraumatic tip, and the like. The guidewire 54 may optionally include a hydrophilic coating over part or all of the guidewire 54, as discussed previously with respect to FIG. 4.

The coated hypotube 46 (FIG. 8) may also be used in medical devices such as catheters. Turning now to FIG. 11, a portion of a catheter 56 is illustrated. FIG. 12 is an axial cross-section taken along line 12-12 of FIG. 11. In FIG. 12, the catheter 56 can be seen to include the coated hypotube 46 bearing the coating 52, as previously discussed. It can be seen that the coating 52 covers at least some of the surface elements 50 while leaving at least some of the radially aligned voids 48 uncovered.

In some embodiments, as illustrated, the catheter 56 may include an optional outer hydrophilic layer 32 over the coated hypotube. In other embodiments, the catheter 56 may include an optional inner polymeric layer 36. The inner polymeric layer 36 may be included to provide a smooth, low-resistance lumen suitable for passing a guidewire or other medical device and may be formed of any suitable material as discussed with respect to FIG. 6. In yet other embodiments, the catheter may optionally include both an outer hydrophilic layer 32 and inner polymeric layer 36.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

We claim:

1. A medical device comprising:
    a hypotube micromachined to include a plurality of slots along substantially the entire length thereof wherein the slots are substantially perpendicular to the axial direction of the hypotube with adjacent slots having distal ends that are substantially semicircular in shape and project in opposite directions along a circumference of the hypotube, the hypotube having a level of flexibility; and
    a tie layer disposed about the entire length of the exterior of the hypotube such that the medical device has a level of flexibility at least substantially equivalent to the level of flexibility of the hypotube.

2. The medical device of claim 1, wherein the hypotube comprises an outer surface and a plurality of radially aligned voids arranged within the outer surface.

3. The medical device of claim 2, wherein the tie layer is in contact with the outer surface of the micromachined hypotube and comprises a continuous layer.

4. The medical device of claim 3, wherein the tie layer comprises an elastomeric polymer.

5. The medical device of claim 2, wherein the tie layer is in contact with the outer surface of the micromachined hypotube and comprises a discontinuous layer.

6. The medical device of claim 5, wherein at least some of the radially disposed voids are not covered by the discontinuous layer.

7. The medical device of claim 1, wherein the micromachined hypotube comprises a nickel/titanium alloy.

8. The medical device of claim 1, wherein the tie layer has an outer surface, and the medical device further comprises a hydrophilic coating disposed on the outer surface of the tie layer.

9. The medical device of claim 1, wherein the micromachined hypotube comprises an inner surface, and the medical device further comprises an inner polymeric layer disposed on the inner surface of the micromachined hypotube.

10. The medical device of claim 1, comprising a catheter.

11. The medical device of claim 1, comprising a guidewire.

* * * * *